United States Patent
Rigassi-Dietrich

(10) Patent No.: US 8,329,201 B2
(45) Date of Patent: Dec. 11, 2012

(54) PROCESS FOR MAKING MULTIPARTICULATES USING A ROLLER COMPACTOR

(75) Inventor: Petra Gisela Rigassi-Dietrich, Therwil (CH)

(73) Assignee: Novartis AG, Basel (CH)

( * ) Notice: Subject to any disclaimer, the term of this patent is extended or adjusted under 35 U.S.C. 154(b) by 875 days.

(21) Appl. No.: 12/301,337

(22) PCT Filed: Jun. 5, 2007

(86) PCT No.: PCT/EP2007/055539
§ 371 (c)(1),
(2), (4) Date: Nov. 18, 2008

(87) PCT Pub. No.: WO2007/141282
PCT Pub. Date: Dec. 13, 2007

(65) Prior Publication Data
US 2010/0003318 A1    Jan. 7, 2010

Related U.S. Application Data

(60) Provisional application No. 60/804,104, filed on Jun. 7, 2006.

(51) Int. Cl.
*A01N 25/34* (2006.01)

(52) U.S. Cl. .................................................. 424/408
(58) Field of Classification Search ................. None
See application file for complete search history.

(56) References Cited

U.S. PATENT DOCUMENTS
5,332,519 A    7/1994    Mazzola

FOREIGN PATENT DOCUMENTS
| EP | 0602014 | 6/1994 |
| WO | 97/36968 | 10/1997 |
| WO | 00/77050 | 12/2000 |

OTHER PUBLICATIONS

Lee et al, Arch. Pharmacal Res. 28 (5), 619 (May 2005).*

* cited by examiner

*Primary Examiner* — James Martinell
(74) *Attorney, Agent, or Firm* — Carmella A. O'Gorman

(57) ABSTRACT

A process for manufacturing multiparticulate pharmaceutical compositions using a roller compactor. The process is particularly useful for producing minitablets without the need of the use of a tablet press. The roller compactor features rolls having depressions or molds in the surface. Upon compaction of pharmaceutical blend, the minitablets are formed by the depressions in the roller surfaces.

3 Claims, 2 Drawing Sheets

PROCESS FOR MAKING MULTIPARTICULATES USING A ROLLER COMPACTOR

This application claims benefit of U.S. Provisional Application No. 60/804,104, filed Jun 5, 2007, which in its entirety is herein incorporated by reference.

FIELD OF THE INVENTION

The present invention relates to a process for making multiparticulates of a therapeutic compound. The process features the use of a roller compactor.

BACKGROUND OF THE INVENTION

Multiparticulates are established dosage forms that include multiple particles in which the aggregate of the particles represents the intended therapeutically useful dose of a therapeutic compound. After oral ingestion, the multiparticulates disperse in the gastrointestinal system to maximize absorption while minimizing side effects. Multiparticulates can be further processed into solid oral dosage forms, such as capsules, tablets and the like.

Alternatively multiparticulates can be directly administered without further processing as multiparticles, microparticles, minitablets, pellets, or beads.

A particularly useful type of multiparticulates is minitablets. Minitablets have a distinct shape and surface area which makes them particularly compatible with film coats, especially functional coatings. Traditionally, minitablets have been made from powder and/or granulate pharmaceutical blends on tablet presses. For example, rotary tablet presses with multiple compression stations may be used to press minitablets with exemplary output rates of about two million units per hour on production scale equipment.

Roller compactors, or chilsonators, are commonly used for dry granulation processes. A roller compactor forces fines, from a pharmaceutical blend, between rotating rollers in order to compact and densify the powders into a smaller volume forming a compact or sheet. The compacts or sheets are subsequently milled to form granules which may then be compressed into tablets.

The present invention features the use of roller compactors to directly form multiparticulates without the need of the use of a separate tablet press or tableting apparatus. Roller compactors allow the opportunity for a continuous production method rather than a batchwise process as found with tablet presses.

SUMMARY OF THE INVENTION

The present invention features a process for manufacturing multiparticulate pharmaceutical compositions. The process features compacting a pharmaceutical blend in a roller compactor that has counterrotating rolls. The roller surfaces have depressions or molds to size and shape the blend into multiparticulate compacts. The resulting multiparticulates can be in the form of multiparticles, microparticles, microtablets, minitablets, pellets or beads. Such multiparticulates have particle sizes greater than 0.5 mm but less than 10 mm. Furthermore, in an uncoated state, the multiparticulates have an individual weight of from about 3 mg to about 10 mg. In an exemplary embodiment, the present process results in minitablets having an individual weight from about 3 mg to about 10 mg, e.g., 4 mg to about 7 mg.

BRIEF DESCRIPTION OF THE DRAWINGS

The accompanying drawings, which are incorporated in and constitute a part of the specification, illustrate an exemplary embodiment of the present invention.

DETAILED DESCRIPTION OF THE INVENTION

Figure 1:
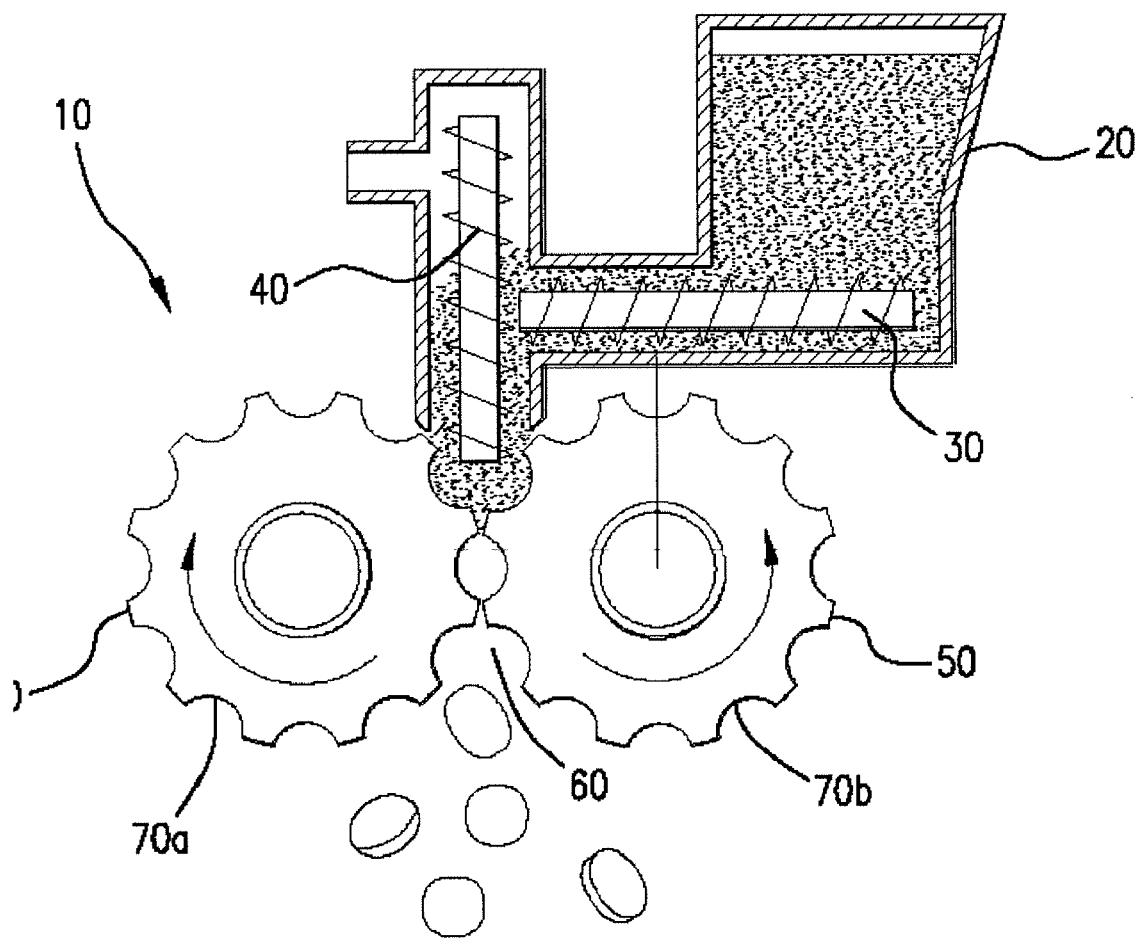
FIG. 1 shows a sectional view of the apparatus used to implement the manufacturing process of the present invention.

The present invention relates to a process for preparing multiparticulate pharmaceutical compositions through the use of a roller compactor.

As used herein the term "pharmaceutical composition" means a mixture containing a therapeutic compound to be administered to a mammal, e.g., a human in order to prevent, treat or control a particular disease or condition affecting the mammal.

As used herein the term "pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

As used herein the term "therapeutic compound" means any compound, substance, drug, medicament, or active ingredient having a therapeutic or pharmacological effect, and which is suitable for administration to a mammal, e.g., a human, in a composition that is particularly suitable for oral administration.

The therapeutic compound(s) is present in the pharmaceutical compositions of the present invention in a therapeutically effective amount or concentration. Such a therapeutically effective amount or concentration is known to one of ordinary skill in the art as the amount or concentration varies with the therapeutic compound being used and the indication which is being addressed. For example, in accordance with the present invention, the therapeutic compound may be present in an amount by weight of about 0.05% to about 99% weight of pharmaceutical composition. In one embodiment, the therapeutic compound may be present in an amount by weight of about 10% to about 95% by weight of the pharmaceutical composition.

As used herein, the term "multiparticulates" refers to drug particles having an average size of greater than 0.5 mm to about 10 mm. By "average particle size" it is meant that at least 50% of the particulates have a particle size of less than about the given value, by weight. The particle size may be determined on the basis of the weight average particle size as measured by conventional particle size measuring techniques well-known to those skilled in the art. Examples of such techniques include, but are not limited to, sedimentation field flow fractionation, photon correlation spectroscopy, light spectroscopy, light scattering and disk centrifugation. Multiparticulates may be multiparticles, microparticles, microtablets, minitablets, or pellets provided that they meet the size dimensions specified above. Note that such multiparticulates do not include granules as known in the art. Granules typically have a particle size of up to 0.5 mm.

Particularly useful forms of multiparticulates are minitablets or pellets, i.e., they are presented and formulated in a form that allows for easy administration of a high load of the therapeutic compound. As used herein, the term "minitablets"

refers to small tablets with an overall weight in their uncoated form of from about 3 mg to about 10 mg, e.g., from about 4 mg to about 7 mg, e.g., about 6 mg. The minitablets may have any shape convenient to one of ordinary skill in the art familiar with making tablets, e.g., spherical, e.g., with a diameter of from about 0.3 mm to about 4 mm, e.g., 1-4 mm or 2-4 mm; or cylindrical, e.g., having a convex upper face and convex lower face and, e.g., with a cylindrical diameter and height which are, independently of each other, of from about 0.5 mm to about 4 mm, e.g., 1-3 mm; or they may be biconvex round minitablets, e.g., whose height and diameter are approximately equal and are from about 0.5 mm to about 4 mm, e.g., 1.5-4 mm, preferably 1.8-2.3 mm, or they may be biconvex or flat square minitablets with rounded corners. Other forms are also possible, e.g., hexagonal, polygonal but also special forms like hearts, half-moons, etc. The minitablets may be uncoated, or coated with one or more layers of coating.

In one exemplary variant the minitablets are uncoated. In another exemplary variant the minitablets may be coated with hydroxypropylmethyl cellulose (HPMC), e.g., HPMC 603 available as, e.g., PHARMACOAT® 603. In yet another exemplary variant the coating(s) include(s) a taste-masking material, e.g., a polyacrylate, preferably an EUDRAGIT®, such as EUDRAGIT®-E or EUDRAGIT®-RD100 or -RS/RL, especially EUDRAGIT®-E. Alternatively, such minitablets may be coated with gastro-resistant coatings. In a further variant they are coated with a third additional coating, e.g., with HPMC or polyethyleneglycols (PEGs) to minimize further any interaction between minitablets and, e.g., a capsule shell or other minitablets. Such third additional coatings may also facilitate the application of colors to the minitablets.

In a further exemplary variant the coating contains is devoid of a plasticizer, such as dibutyl sebacate, or with a plasticizer, such as a fatty acid, such as stearic acid, e.g., stearic acid NF (National Formulary, USP). In yet another exemplary variant they are unencapsulated. In a further exemplary variant they are encapsulated. In a further exemplary variant the encapsulating material gelatin is replaced with alternative hard capsule materials, e.g., HPMC, starch, pullulan or carrageenan. Such coatings may also be used as functional coatings. For example, coatings can be used to alter the release profile of minitablets, such as making the release a sustained, extended, pulsed, delayed or modified release.

In lieu of capsules, the multiparticulates can also be filled into sachets, pouches or stick packs.

Pellets, e.g., typically have a diameter of from 0.2 mm to about 2 mm.

As used herein, the term "modified release form" refers to a formulation which releases the therapeutic compound not immediately, e.g., after disintegration or in case of enteric-coating, i.e., gastro-resistant coating, after stomach passage, but offers a sustained, retard, continuous, gradual, prolonged or pulsatile release and therefore alters drug plasma levels distinctively versus an immediate release formulation. More specifically, the term "modified release formulation" refers to a formulation wherein the therapeutic compound is released and provided for absorption over a longer period of time than from a conventional dosage form, i.e., to a formulation which provides a modified release profile of the therapeutic compound contained therein.

To manufacture such multiparticulate compositions of the present invention, the therapeutic compound may be first blended with pharmaceutically acceptable excipients to form a pharmaceutical powder blend. Examples of such excipients include, but are not limited to, release retardants, plasticizers, disintegrants, binders, lubricants, glidants, stabilizers, fillers and diluents. One of ordinary skill in the art may select one or more of the aforementioned excipients with respect to the particular desired properties of the solid oral dosage form by routine experimentation and without any undue burden. The amount of each excipient used may vary within ranges conventional in the art. The following references which are all hereby incorporated by reference disclose techniques and excipients used to formulate oral dosage forms. See *The Handbook of Pharmaceutical Excipients*, $4^{th}$ edition, Rowe et al., Eds., American Pharmaceuticals Association (2003); and *Remington: the Science and Practice of Pharmacy*, $20^{th}$ edition, Gennaro, Ed., Lippincott Williams & Wilkins (2003).

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 1.5% by weight of composition.

Examples of pharmaceutically acceptable binders include, but are not limited to, starches; celluloses and derivatives thereof, e.g., microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 10-40% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 15% to about 40% by weight of the composition.

Once a blend of therapeutic compound and excipients is obtained, the blend may be compacted in the roller compactor to form multiparticulates, e.g., minitablets.

In traditional roller compaction, the roller compactor apparatus includes multiple rolls, e.g., two counter rotating rolls. As the two counter rotating rolls turn towards each other, material (e.g., the powder blend) is fed into the nip area formed between the surfaces of the rolls. The reduction of volume and the pressure from the nip region causes to material to form a solid compact or sheet. An example of a roller compactor suitable for use in the present invention is equipment from the CHILSONATOR® series from The Fitzpatrick Company (Elmhurst, Ill.). The rolls may have typical diameters of, e.g., 200 or 300 mm with different widths ranging from 50-300 mm.

In the present invention, the surfaces of the two counter rotating rolls are modified. Located on the surface of the two rolls are mutually opposite depressions or molds for receiving and molding the blend. The blend is compacted and pressed (e.g., from 30-300 kN) into a particular shape as formed by the depressions or molds. As the compacted blend exits the roller compactor a multiparticulate, e.g., a minitablet is directly formed. As used herein, "directly" means directly resulting from the compaction in the roller compactor thereby eliminating the need for a separate compaction step in a tablet press.

The curvature of the depressions may be modified to provide for different shaped multiparticulates, or minitablets. Examples of such shapes include, but are not limited to, circular, oval, square or polygonal as previously mentioned. The curvature ensures that there is good separation of the compressed minitablets.

A suitable range of curvature for an exemplary minitablets resulting from the depressions is from about 0.5 mm to about 3 mm, e.g., from about 1-2 mm.

Figure 2:
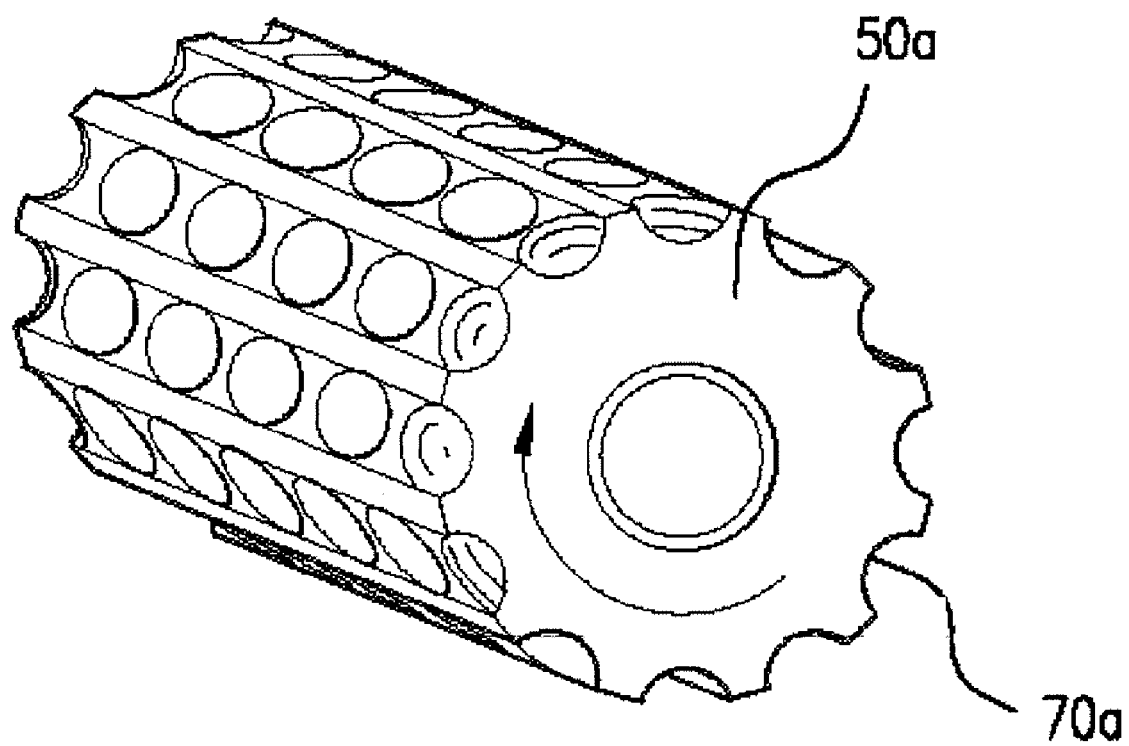
FIG. 2. shows a detailed view of the surface of an exemplary roller for use in the present invention.

FIG. 1 is a schematic showing the parts of an exemplary roller compactor (10). The material to be introduced, e.g., the therapeutic compound and any excipients that are pre-blended, is first added to a hopper 20. The blend is then transferred along a horizontal metering screw 30 to a vertical deaerating, precompression screw 40. Material transfers from the precompression screw into the nip region 60 created between the counter-rotating rolls 50. Located on the surface of each roller 50 are depressions 70. FIG. 2 shows a close up of the surface of an exemplary roller 50a. Each depression, e.g., 70a, on one particular roller 50a has a corresponding depression on the other roller. Each depression corresponds to the shape of one half of the required multiparticulate, e.g., minitablet. When the corresponding depressions, 70a and 70b, meet at the nip region 60, the multiparticulate is molded in the contacted region between the depressions 70a and 70b. Each depression 70 on each roller 50 provides an identically shaped half of the multiparticulate so that the resulting multiparticulate is, e.g., symmetrical. Thus, a blend enters the exemplary roller compactor, and multiparticulates exit the roller compactor. The resulting multiparticulates do not need to be further milled or granulated. Furthermore the resulting multiparticulate are uniformly sized and shaped as produced by the depressions in the roller surfaces.

On a roller with a standard diameter of 200 mm and a roller width of 50-150 mm the depressions can be configured as follows: 100 rows (in a radial direction) with 25-75 molds (in an axial direction). The speed of rotation for the roller is from 5-20 rpm at a lab scale and greater than 50-fold at a production scale. Thus, the use of the processes of the present invention may result in output rates of approximately 0.25-10 million units per hour for lab scale equipment and may result in more than 300 million units per hour for production scale equipment.

To smooth the surface of the minitablets during manufacture, the roller may have special surface coatings, e.g., polytetrafluroethylene (PTFE), chromium nitride, or chromium alloy coatings as known in the art. Such coatings on the roller reduce any sticking of the minitablets to the roller surface. Additionally, standard equipment as known in the art for deburring and/or dedusting can be used to smooth the surface of such multiparticulates.

The exemplary process of the present invention does not require the use of heat and/or solvents. However, heat, cold and/or solvents may be optionally used. Thus, the exemplary process of the present invention may be conducted at or above or below room temperature of the rolls.

Once the multiparticulates are obtained, they can be optionally coated with a functional or non-functional coating as known in the art. Examples of coating techniques include, but are not limited to, sugar coating, film coating, microencapsulation and compression coating. Types of coatings include, but are not limited to, enteric coatings, sustained release coatings, controlled-release coatings.

The utility of all the pharmaceutical compositions of the present invention may be observed in standard clinical tests in, e.g., known indications of drug dosages giving therapeutically effective blood levels of the therapeutic compound; e.g., using dosages in the range of 2.5-500 mg of therapeutic compound per day for a 75 kg mammal, e.g., adult and in standard animal models.

The present invention provides a method of treatment of a subject suffering from a disease, condition or disorder treatable with a therapeutic compound comprising administering a therapeutically effective amount of a pharmaceutical composition of the present invention to a subject in need of such treatment.

The following examples are illustrative, but do not serve to limit the scope of the invention described herein. The examples are meant only to suggest a method of practicing the present invention.

Standard powder blends as known in the pharmaceutical industry are particularly useful in the present invention. An example of a standard powder blend can be a blend of lactose and microcrystalline cellulose in equal parts with 0.5% by weight of the composition of a lubricant (e.g., magnesium stearate).

It is understood that while the present invention has been described in conjunction with the detailed description thereof that the foregoing description is intended to illustrate and not limit the scope of the invention, which is defined by the scope of the following claims. Other aspects, advantages and modifications are within the scope of the claims.

What is claimed:

1. A process for making pharmaceutical minitablet compositions comprising the steps of adding a pharmaceutical blend comprising a therapeutic compound and at least one pharmaceutically acceptable excipient into a roller compactor having a plurality of counter-rotating rolls wherein each roll has a plurality of depressions that correspond to identically shaped depressions on a counter-rotating roll for receiving said blend and compacting said blend between said counter-rotating rolls to directly form symmetrical minitablets without the need for a separate compaction step, the minitablets having an individual weight from about 3 mg to about 10 mg when uncoated.

2. The process of claim 1, wherein said minitablets have an individual weight from about 4 mg to about 7 mg when uncoated.

3. The process of claim 1 or 2, wherein said minitablets have an individual radius of curvature of from about 0.5 mm to about 3 mm.

* * * * *